(12) United States Patent
Carlson

(10) Patent No.: US 8,303,642 B1
(45) Date of Patent: Nov. 6, 2012

(54) METAL INJECTION MOLDED TUBING FOR DRUG ELUTING STENTS

(75) Inventor: James M. Carlson, Gilroy, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1970 days.

(21) Appl. No.: 10/444,277

(22) Filed: May 23, 2003

(51) Int. Cl.
*A61F 2/06* (2006.01)

(52) U.S. Cl. .................... 623/1.15; 623/1.42

(58) Field of Classification Search ......... 623/1.39, 623/1.42–1.54, 23.64, 23.66, 23.7, 1.15; 604/8
See application file for complete search history.

(56) References Cited

U.S. PATENT DOCUMENTS

| | | | |
|---|---|---|---|
| 5,412,608 A * | 5/1995 | Oyama | 365/218 |
| 5,562,725 A * | 10/1996 | Schmitt et al. | 623/1.53 |
| 5,690,644 A | 11/1997 | Yurek et al. | |
| 5,843,172 A | 12/1998 | Yan | |
| 6,071,305 A * | 6/2000 | Brown et al. | 623/1.43 |
| 6,273,913 B1 | 8/2001 | Wright et al. | |
| 6,287,628 B1 * | 9/2001 | Hossainy et al. | 427/2.3 |
| 6,380,457 B1 | 4/2002 | Yurek et al. | |
| 6,395,326 B1 * | 5/2002 | Castro et al. | 427/2.24 |
| 6,709,465 B2 * | 3/2004 | Mitchell et al. | 623/23.7 |
| 6,755,855 B2 | 6/2004 | Yurek et al. | |
| 2002/0007209 A1 * | 1/2002 | Scheerder et al. | 623/1.15 |
| 2002/0082680 A1 * | 6/2002 | Shanley et al. | 623/1.16 |

OTHER PUBLICATIONS

Brochure: *Metal Injection Molding*, Injectamax Corp. Undated.
Brochure: *About Injectamas*, Injectamax Corp., Undated.

* cited by examiner

*Primary Examiner* — Christopher D Koharski
*Assistant Examiner* — Christopher D Prone
(74) *Attorney, Agent, or Firm* — Fulwider Patton LLP

(57) ABSTRACT

An intravascular stent is formed by utilizing the process of metal injection molding (MIM) applied to metal powder, ceramic powder and ceramic metal composite powder. The devices may have longitudinal/circumferential channels and/or depots molded into the tubing thereof to enable such devices to act as a functional drug delivery vehicle having adequate drug reservoir capability.

20 Claims, 8 Drawing Sheets

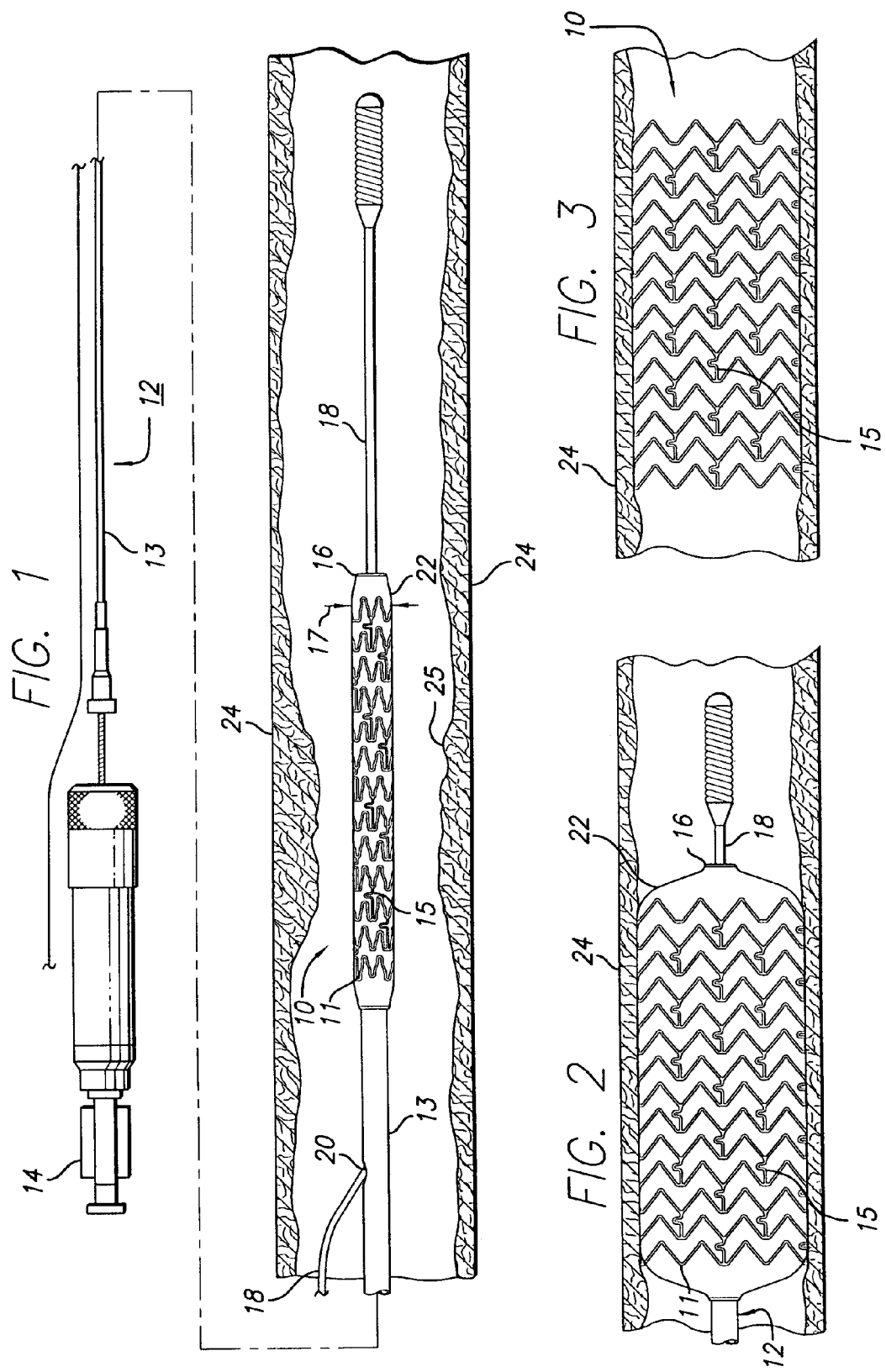

METAL INJECTION MOLDED TUBING FOR DRUG ELUTING STENTS

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels. More particularly, the invention concerns apparatus and methods of manufacturing tubing for the subsequent manufacture into drug-eluting stents, utilizing the process of metal injection molding (MIM) applied to biocompatible metals and metal alloys, ceramics, and ceramic-metal composite materials. These devices may have longitudinal/circumferential channels and/or depots directly molded into the tubing thereof to enable such devices to act as functional drug delivery vehicles having adequate drug reservoir capabilities.

Intravascular interventional devices such as stents are typically implanted within a vessel in a contracted state, and expanded when in place in the vessel in order to maintain the patency of the vessel to allow fluid flow through the vessel. Stents have a support structure such as a metallic structure to provide the strength required to maintain the patency of the vessel in which it is to be implanted, and are typically provided with an exterior surface coating to provide a biocompatible and/or hemocompatible surface. Since it is often useful to provide localized therapeutic pharmacological treatment of a blood vessel at the location being treated with the stent, it is also desirable to provide intravascular interventional devices such as stents with a biocompatible and/or hemocompatible surface coating of a polymeric material with the capability of being loaded with therapeutic agents, to function together with the intravascular devices for placement and release of the therapeutic drugs at a specific intravascular site.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty. Restenosis is the normal reaction of the human body to a foreign body being implanted in one of the coronary, carotid, or peripheral arteries. The coating of bare metal stents with an anti-cancer drug is the current approach being considered in order to decrease or eliminate restenosis. However, current design and fabrication methods for drug-eluting stent devices are not optimal. Accordingly, various limitations exist with respect to such current design and fabrication methods for drug-eluting stents.

One significant limitation, for example, is that current designs for drug-eluting stents fail to provide for uniform drug distribution in the artery. Since uniformity is dictated by metal stent skeletal structure, increasing uniformity by increasing the metal stent surface area makes the stent stiff and compromises flexibility and deliverability. Additionally, current device designs incorporate expandable ring elements and connectors, which are then coated using a polymer plus drug coating or loaded with microreservoirs of drug. The expandable nature of the rings limits the extent of uniformity in coverage and drug distribution that can be achieved. Further limitations include the mixture of the drug in a polymer and/or solvent solution which is then spray coated on the entire stent surface with a primer, drug, and topcoat layers being used to control release kinetics. This approach tends to cause cracking in the drug-coating layer, since the layer also undergoes stretching during stent expansion, and resultant considerable washout of the drug into the blood stream, and only a fraction gets into the tissue/artery. Further, the amount of the drug that can be loaded on the stent is limited by mechanical properties of the coating, since the higher drug content in the polymer makes the coating more brittle and causes cracking thereto. Therefore, loading a higher drug dose requires coating with more polymer on the device. Other limitations in current fabrication methods of drug-eluting stents include the necessity of several coating steps along the length of the stent which is time consuming. Special equipment for crimping the drug-eluting stent on the balloon and to securely attach the stent on the balloon is also needed in accordance with current fabrication methods in order to prevent damage to the coating. As conventional spray coating is capable of programming only one drug release rate kinetics, variation of drug dosing and release kinetics along the length of the stent is not possible using the current coating process.

Several challenges face the major medical device manufacturing companies in regard to implementing a drug-eluting stent into the marketplace. A common method of applying an anti-cancer drug is to first apply a polymer primer layer to the bare metal stent, dissolve the drug into a suitable polymer using a suitable solvent, spray the drug-polymer mixture onto the primer layer, and then apply a polymer topcoat. One particular challenge facing medical device manufacturers is reducing the usage of such polymers. Medical device manufacturing companies are also faced with the challenge of making drug-eluting stents that have adequate drug storage capability. The creation of channels and/or depots into tubing using laser machining is one approach that has been considered to resolve this issue. However, it has been found that laser machining requires more control (i.e., consistency) in order to be a reliable and controlled manufacturing process. For example, in forming depots using laser machining, the depth thereof is not precisely repeatable from one depot to the next. Further, studies have shown that the use of laser machining in creating channels and/or depots into tubing is not a cost effective way to manufacture high volumes of components with intricate geometric shapes and designs at a competitive price.

What has been needed and heretofore unavailable in the art is a method of manufacturing tubing for the subsequent manufacture into drug-eluting stents that would increase the reservoir capacity of the stent by incorporating longitudinal and/or circumferential channels and geometrically-shaped depots into the abluminal surface of the tubing. Thus, it would be desirable to have a drug-eluting stent that is optimally designed to have increased drug storage capability, which improves the reproducibility of drug storage features currently being manufactured by the process of laser machining, hence eliminating the need for post laser machining of such channels and/or depots. The present invention meets these and other needs.

SUMMARY OF THE INVENTION

The present invention is directed to intravascular stents having drug-eluting capabilities made from tubing formed by the manufacturing process of metal injection molding (MIM). Methods for making the same are also disclosed herein. In particular, these devices include longitudinal and/or circumferential channels and/or depots formed into the tubing thereof by application of MIM processes to enable such devices to act as functional drug delivery vehicles having adequate drug reservoir capabilities.

The drug-eluting stent manufactured in accordance with the present invention can be readily delivered to the desired body lumen, such as a coronary or carotid artery (peripheral vessels, bile ducts, etc.), by mounting the drug-eluting stent on an expandable member of a delivery catheter, for example a balloon, and advancing the catheter and drug-eluting stent assembly through the body lumen to the target site. Generally, the drug-eluting stent is compressed or crimped onto the balloon portion of the catheter so that the drug-eluting stent does not move longitudinally relative to the balloon portion of the catheter during delivery through the arteries, and during expansion of the drug-eluting stent at the target site. The drug-eluting stent is relatively flexible along its longitudinal axis to facilitate delivery through tortuous body lumens yet is stiff and stable enough radially in an expanded condition to maintain the patency of a body lumen such as an artery when implanted therein.

In one aspect of the invention, an intravascular stent for controlled storage and release of therapeutic drugs and for delivery of the therapeutic drugs in localized drug therapy in a blood vessel is disclosed. Specifically, a pattern of circumferential rings are interconnected by links having a longitudinal axis. The rings and links are formed from tubing by subjecting a base material to the MIM process such that the tubing has an inside diameter and an outside diameter and a plurality of longitudinal channels arranged circumferentially around thereof which set parallel to the stent longitudinal axis. The base material may be a metallic powder, a ceramic powder, or a ceramic-metal composite powder. Possible metallic powders include stainless steel, nitinol and cobalt-chromium alloy. A possible ceramic is carbide while a possible ceramic-metal composite is tungsten-carbide. To aid in stent visibility the base material may include an element or alloy sufficiently radiopaque for x-ray imaging such as tantalum, titanium, tungsten or vanadium or an element which is magnetic resonance imaging (MRI) compatible. The mixture is then injected into a geometric die configured to form a tubing having a nonuniform outside diameter and a substantially uniform inside diameter. The material is then subjected to standard MIM processes including mixing, molding, debinderizing, and sintering. In one particular aspect, a plurality of longitudinal channels arranged circumferentially around the tubing and set parallel to the longitudinal axis may be molded within an outside surface of the tubing. The plurality of longitudinal channels molded into the tubing have a wall which at least partially encapsulates a therapeutic drug stored therein.

In various aspects of the present invention, the plurality of longitudinal channels molded into the outside surface of the tubing can assume various configurations such as a four, six or eight channel design. For a four channel design, the longitudinal channels are set ninety degrees apart while being circumferentially arranged around the tubing. A six channel design is configured such that the longitudinal channels are set sixty degrees apart. In a further detailed aspect, an eight channel design is configured such that the longitudinal channels are set forty-five degrees apart. Regarding dimensions of the aforementioned longitudinal channels, the channels have a thickness and a width that can be accordingly modified in order to increase storage of the therapeutic drug therein.

In another aspect of the present invention, the tubing may have a combination of longitudinal channels and depots molded therein. Depots are molded into at least a section of an outside surface of the tubing. Possible geometrical shapes that may be assumed by the depots, include, but are not limited to, circular, square, rectangular, trapezoidal, and triangular shapes. Depots may have a depth of about one half the thickness of the tubing or about 0.002 inch (0.050 mm).

In a further aspect of the present invention, the tubing may have a plurality of circumferential channels molded therein, which are arranged around the tubing while being perpendicular to the longitudinal axis. Another aspect of the present invention includes a combination of longitudinal channels and circumferential channels molded into the tubing pursuant to MIM technology. In a detailed aspect, a plurality of depots may be molded into at least a section of the outside surface of the tubing.

Upon completion of the MIM process, the resultant tubing may be laser cut to create a stent pattern including, but not limited to, circumferential rings interconnected by links. In a detailed facet of the invention, the tubing may be made nanoporous. This is accomplished through the proper selection of the pressure force applied to the base material during molding and the temperature/time elements associated with sintering, in view of the particle size of the base material powder. The pores of the tubing, or the stent formed therefrom, may be impregnated with a drug material.

The therapeutic drug loaded into the longitudinal channels, circumferential channels and/or depots of the present invention stent can include antiplatelets, anticoagulants, antifibrins, antiinflammatories, antithrombins, and antiproliferatives. These foregoing types of therapeutic drugs, used to treat or prevent restenosis, are provided by way of example and are not meant to be limiting, since other types of therapeutic drugs may be developed which are equally applicable for use with the present invention. Furthermore, the calculation of dosages, dosage rates and appropriate duration of treatment are previously known in the art.

It should be appreciated that the present invention stent formed from MIM tubing may be utilized in any part of the vasculature including neurological, carotid, coronary, renal, aortic, iliac, femoral, or other peripheral vasculature.

An additional aspect of the present invention provides for a method of making an intravascular stent having enhanced drug reservoir capabilities. One method of making the stent involves mixing a base material with a binding material to form a mixture. The mixture is then molded by injecting the mixture into a geometric die, which is configured to form a tubing having inside and outside diameters and a plurality of longitudinal channels arranged circumferentially around the tubing while being parallel to a longitudinal axis. A pressure force is then subsequently applied to the mixture. The method is continued by proceeding with standard MIM processes including the steps of debinderizing and sintering. Upon completion of the MIM processes, a stent pattern can be formed from the tubing that includes circumferential rings interconnected by links. The plurality of longitudinal channels can be loaded with at least one therapeutic drug.

In a further aspect of the present invention, the method of making an intravascular stent having enhanced drug reservoir capabilities may include molding the mixture by injecting the mixture into the geometric die, which is configured to form a tubing having inside and outside diameters and a plurality of longitudinal channels and circumferential channels arranged around the tubing. The remaining steps of the standard MIM process are carried out as set forth in the preceding embodiment. In a detailed aspect of the invention, a plurality of depots may be molded into the MIM tubing to further increase the drug reservoir capabilities of the stent.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a stent embodying features of the invention which is mounted on a delivery catheter and disposed within a damaged artery;

FIG. 2 is an elevational view, partially in section, similar to that shown in FIG. 1 wherein the stent is expanded within a damaged artery;

FIG. 3 is an elevational view, partially in section, depicting the expanded stent within the artery after withdrawal of the delivery catheter;

DETAILED DESCRIPTION OF THE PREFERRED EMBODIMENTS

Figure 4:
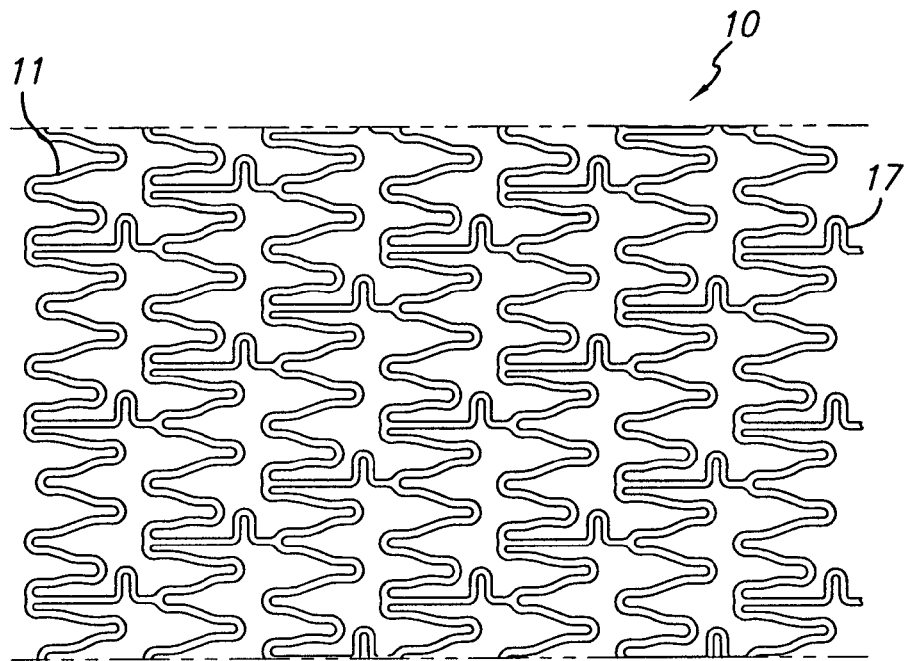
FIG. 4 is a plan view of a flattened stent illustrating the stent pattern of FIGS. 1-3 formed by a plurality of cylindrical rings and undulating links.

The present invention relates to intravascular stents made from tubing formed by the manufacturing process of metal injection molding (MIM). In particular, these devices may have longitudinal and/or circumferential channels and/or depots directly molded into the tubing thereof to enable such devices to act as functional drug delivery vehicles having enhanced drug reservoir capabilities.

With reference to the drawings, FIG. 1 depicts a metallic stent 10 (longitudinal/circumferential channels and/or depots not shown) mounted on a catheter assembly 12 which is used to deliver the stent and implant it in a body lumen, such as a coronary artery, carotid artery, peripheral artery, or other vessel or lumen within the body. The stent generally comprises a plurality of radially expandable cylindrical rings 11 disposed generally coaxially and interconnected by undulating links 15 disposed between adjacent cylindrical elements. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 25 as shown in FIG. 1, or a dissection, or a flap which are commonly found in the coronary arteries, carotid arteries, peripheral arteries and other vessels.

In a typical procedure to implant stent 10, the guide wire 18 is advanced through the patient's vascular system by well known methods so that the distal end of the guide wire is advanced past the plaque or diseased area 25. Prior to implanting the stent, the cardiologist may wish to perform an angioplasty procedure or other procedure (i.e., atherectomy) in order to open the vessel and remodel the diseased area.

Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery.

The stent patterns shown in FIGS. 1-3 are for illustration purposes only and can vary in size and shape to accommodate different vessels or body lumens. Further, the metallic stent 10 is of a type that can be used in accordance with the present invention. FIG. 4 is a plan view of a flattened stent illustrating the stent pattern of FIGS. 1-3 formed by a plurality of cylindrical rings 11 and undulating links 17. The stent 10 is shown in a flattened condition so that the pattern can be clearly viewed, even though the stent is never in this form. The stent is typically formed from a tubular member, however, it can be formed from a flat sheet such as shown in FIG. 4 and rolled into a cylindrical configuration.

Figure 5:
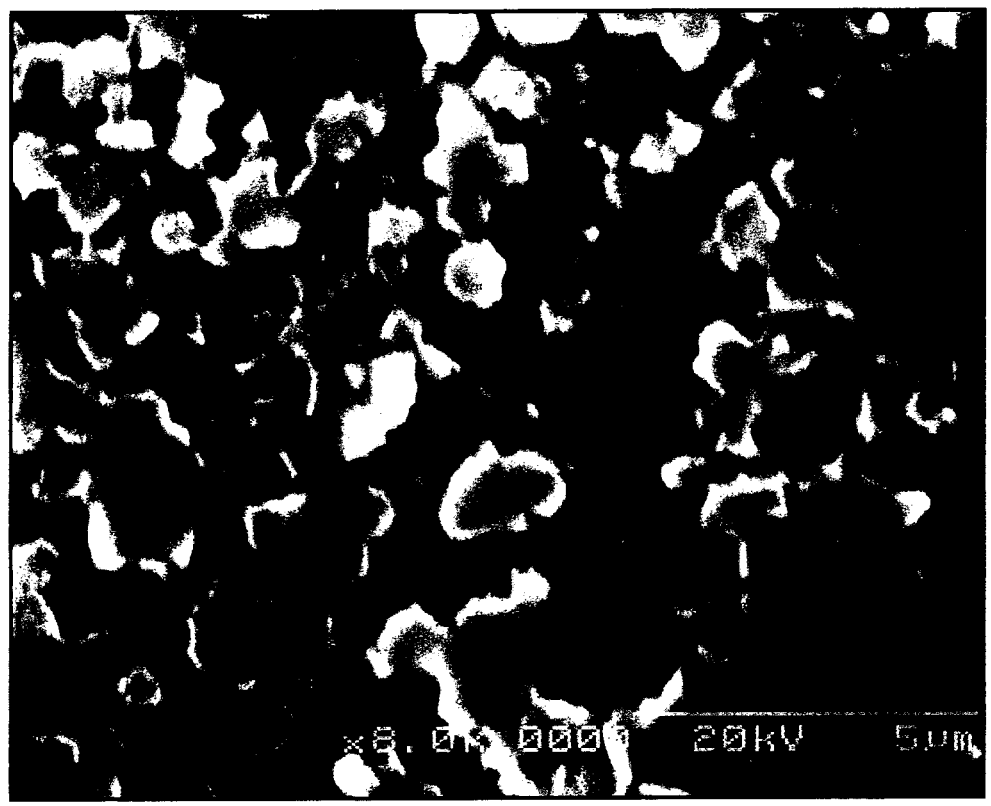
FIG. 5 is a photomicrograph of a metal injection molded (MIM) part in accordance with the present invention detailing the pattern of surface porosity typically present in such type of parts.

FIG. 5 depicts a photomicrograph at 8000× magnification of a metal injection molded part formed in accordance with the present invention. In particular, FIG. 5 shows the pattern of surface porosity typically observed in such MIM parts.

In accordance with the present invention, the tubing from which the stent is made is manufactured using a metal injection molding (MIM) process. Metal injection molding technology produces high quality finished metal components through the molding of metal alloy powder as if it were plastic. Some advantages of using MIM technology for the manufacture of medical devices such as intravascular stents include lower production costs, greater design freedom, and high density finished parts for strength and exacting tolerances. In particular, with the use of MIM technology, product development cycles can be shortened and secondary machining operations eliminated. It is possible to eliminate several finishing steps completely using the MIM process. In short, MIM technology is economical in that it allows for the precise molding of small, intricate designs at low cost. The currently used process in the art requires that depots be laser machined into the stents before or after laser cutting and electropolishing at an additional cost. Further, MIM technology is versatile and nonrestrictive allowing for much greater design freedom and flexibility. The MIM process is particularly suited for small, intricate shapes having a finished part weight of 100 grams or less. Densities up to 99.5% can be achieved through use of MIM. In comparison with other methods, MIM produces smoother surface finishes directly from the mold cavity. MIM is a very exacting technology in that tolerances of +/−0.0005 inch (0.0127 mm) can be achieved. Accordingly, the high tolerances of the MIM process eliminates the inconsistency issues of the currently used laser machining process in the art by improving, the reproducibility of drug storage features incorporated into the stent tubing. The four basic steps for making MIM parts, as further described below, include mixing, molding, debinderizing, and sintering.

MIXING—During the mixing step, a selected base material is hot mixed or otherwise blended with a thermoplastic binder, wax, and lubricant. The base material is usually an extremely fine metallic or ceramic material. The organic binder may be selected from the group including ethylenevinyl acetate copolymer, polyethylene, atactic polypropylene, polystyrene, polybutyl methacrylate, paraffin wax, carnauba wax, or the like. The blending or mixing of the base material with the organic binder may be conducted in accordance with blending methods known in the art. For example, the base material and the organic binder may be hot mixed to produce a thick homogenous blend, which is subsequently cooled and granulated to produce a feedstock. Mixing may be achieved within a pressure type kneader or using a screw-type injection press as is known in the plastics industry.

Mixtures for "green" parts (i.e., materials which have been provided but have not yet been sintered) are typically formed of about 40% thermoplastic powder, about 60% metallic powder, and various additive materials. Various thermoplastic powders used in MIM processes are set forth in Table 2. Metallic powders are typically made by gas atomization or by milling operations as is known in the art. The exact composition of metallic powders used in MIM applications is proprietary in nature. In addition to the thermoplastic powder, the following additive materials (i.e., binders) can be added to the metallic powder to aid in the molding process. A plasticized, cross-linkable thermoplastic polymer is first used so that the mixture mimics a glue during injection. Further, a low viscosity polymer that can be easily removed after molding is added. For example, a water soluble compound such as polyethylene glycol can be used. Various additive materials that are added to the mixture include antioxidants, coupling agents, and internal lubricants such as waxes, surfactants, and flex agents.

MOLDING—Molding is performed in a standard injection molding machine (not shown). In this machine, the preheated feedstock is injected under relatively low pressure into a geometric die. The organic binder in the feedstock makes the mixture flow much more easily thereby ensuring that the corners and undercuts of the mold are sufficiently filled. The fluidity is a function of the type of binder and metallic powder used. The parts are allowed to cool and solidify and are then ejected as intricately shaped parts. These "green" parts are loaded onto fixtures for the remainder of the batch processing.

DEBINDERIZING—The green parts first enter the debinderizer (a low temperature oven), which sequentially removes most of the various binders from the parts by evaporation leaving behind fully oxidized "brown" parts. The debinderizer utilizes high air flow to sweep the parts and mechanical traps to collect condensates. Because of the complex run profile of temperature ramps and soak times, the entire sequence is microprocessor controlled. The green parts can also be debinded by solvent or solvent and temperature means.

SINTERING—The final step is performed by a high temperature process reactor, where the material assumes its final properties and dimensions. A microprocessor controls a complex run profile of temperatures, times, and internal oven atmospheres. A combination of reactive and inert gases is used to tailor the atmosphere to the special requirements of each process sequence. The five basic sequences include purge, decarburization, reduction, sinter, and cool down. During sintering, temperatures approach between 75% and 85% of the base material's melting point. The base material powders diffuse, densification occurs, and the parts shrink. Since the size and the shape of the original powder particles are rigidly controlled, the shrinkage is uniform along all axes and therefore very predictable. As a result, the finished parts retain the original shape of the molded green parts. Shrinkage of the molded parts to their final and fully sintered state ranges from 15% to 25% depending upon what base material is being used. The geometric die is precisely oversized to compensate for shrinkage such that the sintered part shrinks to the desired dimensions.

In accordance with the invention, the base material may be a metallic powder, a ceramic powder or a metal-ceramic composite powder. Examples of possible metallic powders include, but are not limited to, stainless steel, nitinol and cobalt-chromium alloys. In order to enhance the visibility of the tubing, and hence the stent formed therefrom, the metallic powder may include an element or alloy sufficiently radiopaque for x-ray imaging, e.g., fluoroscopy, computed tomography, etc. In this regard, the metallic powder may include, for example, at least one of the following materials such as tantalum, titanium, tungsten, and vanadium.

To further enhance the visibility of the tubing, the metallic powder may include a magnetic resonance imaging (MRI) compatible element or alloy. In this regard, the metallic powder may be formed of an alloy having a relatively higher volume fraction of titanium and a relatively lower volume fraction of an added element, wherein the added element may include tantalum, niobium, zirconium, and hafnium. Alternatively, the added element may be molybdenum, aluminum, tungsten, iridium, platinum, gold, palladium, and silver. The added element may also be yttrium, technetium, ruthenium, rhodium and rhenium. Furthermore, the added element may be selected from a group of the transition metals with the exception of mercury, cadmium, osmium and copper as these are toxic in the bloodstream. As an alternative to metal, the base material may be a ceramic powder or a ceramic-metal composite powder, such as tungsten-carbide or tungsten-carbide/cobalt-chromium.

Table 1 set forth below lists mechanical properties of typical metals manufactured by MIM processes. Each of these alloys may be used in the manufacture of medical devices such as stents.

TABLE 1

Uniaxial Tensile Properties Expected from Metal Injection Molding Process[1-3]

| Alloy | Heat Treatment | 0.2% Offset Yield Strength (ksi) | Ultimate Tensile Strength (ksi) | % Elongation |
|---|---|---|---|---|
| Duplex stainless steel (grade 2205) | As-sintered | 75 | 90 | 27 |
| 17-4 pH stainless steel | As-sintered | 101.2 ± 10.3 | 131 ± 6.6 | 6.5 ± 2.3 |

TABLE 1-continued

Uniaxial Tensile Properties Expected from Metal Injection Molding Process[1-3]

| Alloy | Heat Treatment | 0.2% Offset Yield Strength (ksi) | Ultimate Tensile Strength (ksi) | % Elongation |
|---|---|---|---|---|
| 17-4 pH stainless steel | Hardened | 160.7 ± 4.2 | 175.1 ± 10.5 | 7.3 ± 2.8 |
| 316L stainless steel | As-sintered | 30.3 ± 5.4 | 77 ± 3.6 | 51.3 ± 5.8 |
| 304L stainless steel | As-sintered | 23.1 ± 5.1 | 69.8 ± 4.2 | 53.3 ± 15.3 |
| 440C stainless steel | Hardened | 235 | 242 | 2 |
| 430L stainless steel | As-sintered | 33.1 ± 2.7 | 51.1 ± 14.3 | 33.3 ± 14.4 |
| 430L stainless steel | Hardened | 140 | 155 | 7.5 |
| 420 stainless steel | Hardened | 208 ± 13.2 | 251.3 ± 13 | 5.3 ± 3.2 |
| 410L stainless steel | Hardened | 157.5 | 200 | — |
| 630 PH stainless steel | Hardened | 158 | 172 | 6 |
| XM19 stainless steel | | 25 | 70 | — |
| Tungsten heavy alloy | As-sintered | 97 | 110 | 5 |
| Kovar (ASTM F-15) | As-sintered | 48.6 | 68.2 | 30 |
| CP Titanium | As-sintered | 55.2 | 83.4 | 15.5 |
| L-605 (ASTM F-90) | As-sintered | 56.7 | 118.3 | 25.5 |
| Co—28Cr—6Mo | As-sintered | 75 | 145 | 40 |
| Ti—6Al—4V | As-sintered | 116 | 132 | 11 |
| Nitinol | As-sintered | 23.2 | 65.3 | 30 |
| Fe—2Ni | As-sintered | 31.9 | 65.3 | 15 |
| Fe—2Ni | Hardened | 203 | 232 | 1 |
| Fe—8Ni | As-sintered | 72.5 | 137.8 | 5 |
| Fe—8Ni | Hardened | 188.5 | 261.1 | 2 |
| Fe—3Si | — | 55.1 | 79.8 | 20 |

[1]Data was obtained from MIM manufacturer websites.
[2]K. F. Hens, "Metal Injection Molding: Enhanced Processes Offer High-Precision Results", *Medical Device & Diagnostic Industry*, November 2000, pp. 83-85.
[3]J. L. Johnson, "Mass Production of Medical Devices by Metal Injection Molding", *Medical Device & Diagnostic Industry*, November 2002, pp. 48-53.

The alloys set forth in Table 1 can be manufactured using the following thermoplastic binders in Table 2.

TABLE 2

Possible Formulations of Metallic Powder (Atomized or Milled Form) and Thermoplastic Binder

| Alloy | Amount of Metallic Powder (wt. percent) | Amount of Thermoplastic Powder (wt. percent) |
|---|---|---|
| Duplex stainless steel (grade 2205) | 60 | 40 Acetal |
| 17-4 pH stainless steel | 65 | 35 Nylon 6/6 |
| 316L stainless steel | 60 | 40 Polypropylene |
| 304L stainless steel | 65 | 35 Polycarbonate |
| 440c stainless steel | 60 | 40 ABS (Acronitrile Butadiene Styrene) |
| 430L stainless steel | 65 | 35 Polycarbonate and ABS Blend |
| 420 Stainless Steel | 60 | 40 Polyethermide |
| 410L Stainless Steel | 65 | 35 Polybutylene Terephtalate |
| 630 pH Stainless Steel | 60 | 40 Polystyrene |
| XM19 Stainless Steel | 65 | 35 Polyurethane |
| Tungsten Heavy Alloy | 60 | 40 Thermoplastic Elastomer |
| Kovar (ASTM F-15) | 65 | 35 Acrylic |
| CP Titanium | 60 | 40 Acetal |
| L-605 (ASTM F-90) | 65 | 35 Nylon 6/6 |

TABLE 2-continued

Possible Formulations of Metallic Powder
(Atomized or Milled Form) and Thermoplastic Binder

| Alloy | Amount of Metallic Powder (wt. percent) | Amount of Thermoplastic Powder (wt. percent) |
|---|---|---|
| Co—28Cr—6Mo | 60 | 40 Polypropylene |
| Ti—6Al—4V | 65 | 35 High Density Polypropylene (HDPE) |
| Fe—2Ni | 60 | 40 Polycarbonate |
| Fe—8Ni | 65 | 35 Acronitrile Butadiene Styrene (ABS) |
| Fe—3Si | 60 | 40 Polyethermide |

Figure 6:
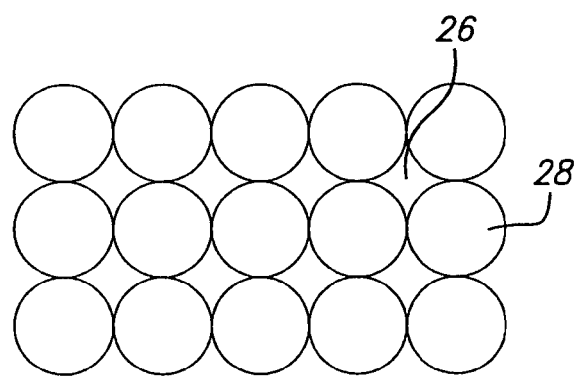
FIG. 6 is a planar view of particles of base material used to form tubing by a MIM process.

In one embodiment of the present invention, the tubing is sintered to near 100% density using a suitable temperature/time that is a function of the base material. In other embodiments of the present invention, the tubing may be sintered to a lesser density in order to form nanoporous tubing. The nanoporosity of the tubing is a function of the particle size of the base material powder, the molding force and the temperature/time characteristics of the sintering process. Referring to FIG. 6, the base material powder is generally selected to have a particle size of about 1 to 10 nanometers; accordingly, there are minute gaps 26 between adjacent particles 28. These gaps form the pores of the tubing. After being injection molded, the particles compress under the molding force and the gaps between adjacent particles reduce in size. As the final step of the MIM process, the sintering process causes portions of adjacent particles to join thereby reducing the size of the pores. Accordingly, the size of the resultant pores may be controlled by selecting the appropriate particle size of the base material (smaller size particles produce smaller pores), the molding force (a higher force produces smaller pores) and the temperature of sintering (a higher temperature in combination with a longer time produces smaller pores). The porosity of the metal injection molded tubing used in the manufacture of the present invention stent ranges from about 92% to about 99% dense. There is about a one to ten micron hole size between the metal grains of the MIM tubing.

Figure 7:
FIG. 7 is a schematic illustration of a micro-channel finite element analysis model in accordance with the present invention.
Figure 8:
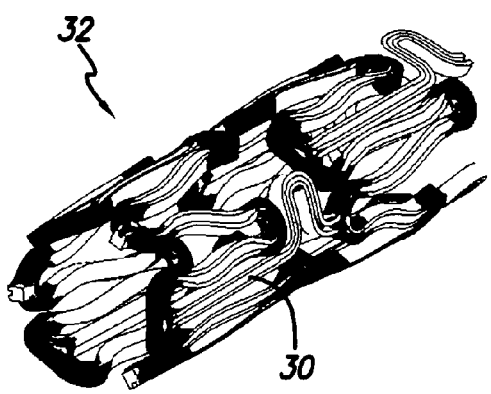
FIG. 8 is a schematic illustration of the micro-channel finite element analysis model of FIG. 7 showing the plastic strain contour at crimp in accordance with the present invention.
Figure 9:
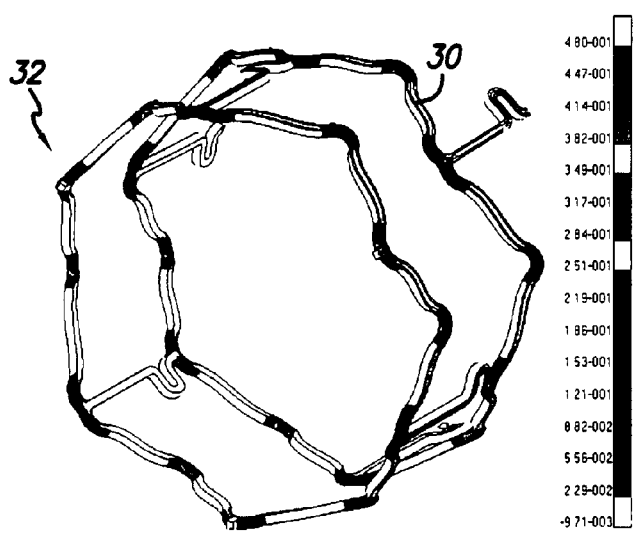
FIG. 9 is a schematic illustration of the micro-channel finite element analysis model of FIG. 7 showing the plastic strain contour at expansion in accordance with the present invention.

FIGS. 7-9 illustrate various configurations (i.e., at crimp and at expansion) of metal injection molded micro-channels 30 formed within tubing subsequently manufactured into a pattern similar to an ACS VISION® (manufactured by Advanced Cardiovascular Systems, Inc. of Santa Clara, Calif.) stent 32 made from a cobalt chromium alloy. As set forth in Table 3, use of a 360 degree model stent having a channel width that is 50% of the strut width at the links and bar arms, in addition to a channel width that is 33% of the strut width at crests and filled with polymer, yields a 60% maximum failure strain. Results from finite element analysis (FEA) tests performed on the metal injection molded micro-channels of a micro-channel model (Table 3) are set forth in Table 4. Accordingly, it is clear from the FEA tests that a stent having a channel depth of 25% and 50% of the strut radial thickness at maximum strain at crimp has substantially the same structural characteristics as that of a standard stent having no such channels. Likewise, the FEA tests further reveal that a stent having a channel depth of 25% and 50% of the strut radial thickness at maximum strain at expansion yields a comparable strain result as compared to a standard stent having no such channels. Specifically, when the channel depth is 25% of the radial strut thickness the lowest fatigue safety factor is unaffected by the existence of the channel. When the channel depth is 50% of the strut radial thickness the fatigue safety factor decreases by 13% for a high pressure load case (default) and decreases by 22% for a low pressure load case.

TABLE 3

Micro-Channel Finite Element Analysis Model

| Model description | Channel width | Channel filler | Maximum failure strain |
|---|---|---|---|
| 360 degree model | 50% strut width at links and bar arms; 33% strut width at crests | Filled with polymer with E = 30 ksi ($E_{CoCr}$ = 30 ksi) | 60% |

TABLE 4

Micro-Channel Finite Element Analysis Model

| 360 degree model | No channel | Channel depth = 25% t (strut radial thickness) | Channel depth = 50% t (strut radial thickness) |
|---|---|---|---|
| Maximum strain at crimp % | 11.6 | 11.7 | 11.6 |
| Maximum strain at expansion % | 43.0 | 43.1 | 43.1 |

Figure 10:
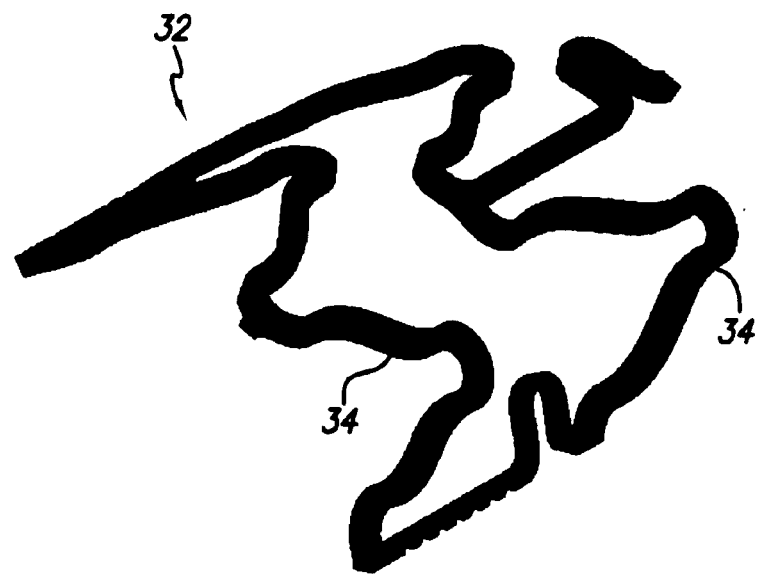
FIG. 10 is a schematic illustration of a micro-depot finite element analysis model in accordance with the present invention.
Figure 11:
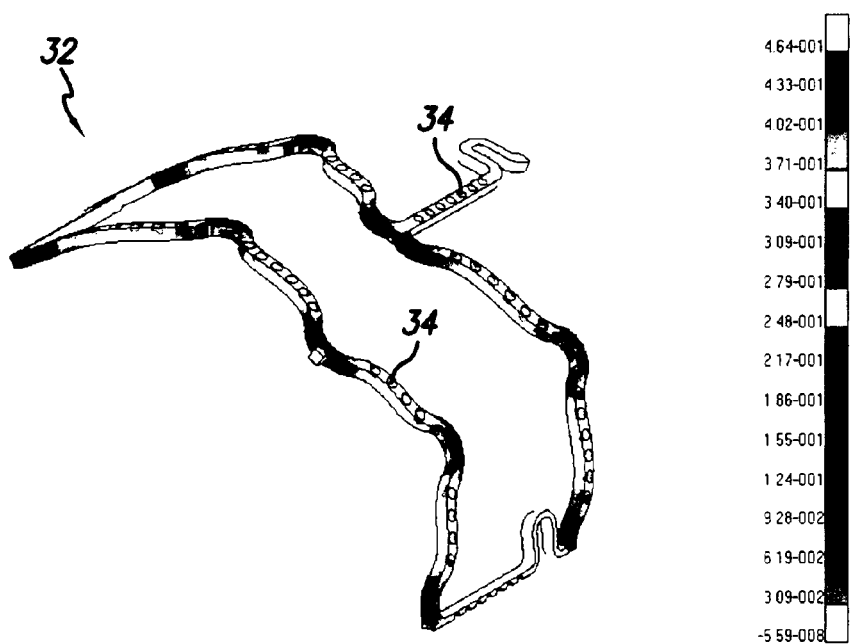
FIG. 11 is a schematic illustration of the micro-depot finite element analysis model of FIG. 10 showing the plastic strain contour at expansion in accordance with the present invention.

FIGS. 10 and 11 illustrate further FEA studies performed on the ACS VISION® stent 32 having micro-depots 34 metal injection molded therein. In particular, based on the expansion analysis, the maximum strains for the depot stent are substantially comparable to those of the standard stent without the depots. FIG. 11 illustrates the model and the plastic strain contour for the ACS VISION® stent at 3.75 mm inner diameter (ID) expansion.

The metal injection molded stent of the present invention may be used in virtually all stent applications, including the carotid, coronary, and peripheral arteries. It is further contemplated by the present invention that the metal injection molded tubing can be used in the subsequent manufacture of stents of virtually any stent design and is not meant to be limited to the designs set forth herein. Accordingly, as set forth in Table 5, the metal injection molded tubing made in accordance with the present invention is designed to have the following strut dimensions for each respective stent model. Each of the listed stent models is manufactured by Advanced Cardiovascular Systems, Inc. of Santa Clara, Calif.

TABLE 5

Stent Strut Thickness and Width Dimensions for
Various Advanced Cardiovascular Systems, Inc. Stents

| Stent Model | Strut Width (in) [mm] | Strut Thickness (in) [mm] |
|---|---|---|
| Multi-Link ® | 0.0038 [0.0965] | 0.0022 [0.0559] |
| Multi-Link Duet ® | 0.0038 | 0.0055 [0.1397] |
| Multi-Link Tetra ® | 0.0038 | 0.0036/0.0049 [0.0914/0.1245] vt |
| Multi-Link Penta ® | 0.0038 | 0.0037/0.0049 [0.0940/0.1245] vt |
| Multi-Link Zeta ® | 0.0038 | 0.0037/0.0049 vt |
| Multi-Link Vision ® | 0.0038 | 0.0032 [0.0813] |

Figure 12:
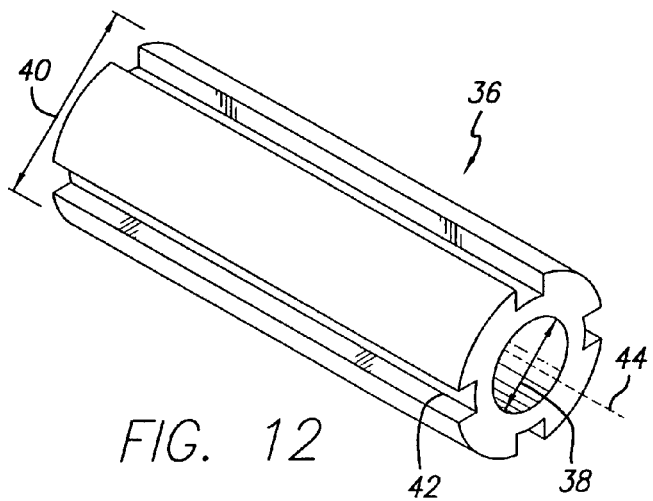
FIG. 12 is a longitudinal, plan view of MIM tubing having four channels arranged ninety degrees apart made in accordance with the present invention.

In one embodiment of the present invention as shown in FIG. 12, the selected base material is subjected to the MIM process set forth above to form a piece of tubing 36 having an inside diameter 38 and an outside diameter 40. A plurality of longitudinal channels 42 are molded in a circumferential manner around the tubing and set parallel to a longitudinal axis 44. In this embodiment, four longitudinal channels may be molded into the tubing such that the channels are positioned approximately ninety degrees apart. As set forth in further detail below, the metal injection molded tubing for this and the following embodiments can be cut into an appropriate stent pattern to form a stent followed by electropolishing in the usual manner. It can be appreciated that the stent is not limited to a ring-and-link design as the stent could also be in the form of a thin metallic sheet in another embodiment.

Figure 13:
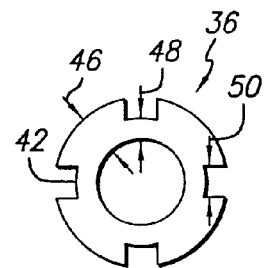
FIG. 13 is an enlarged, transverse, cross-sectional view of the MIM tubing of FIG. 12 made in accordance with the present invention.

FIG. 13 illustrates an enlarged, transverse, cross-sectional view of the MIM tubing of FIG. 12. As shown in FIG. 13, the MIM tubing includes various dimensions such as a radial thickness 46 in a range of from about 0.010 inch (0.254 mm) up to about 0.020 inch (0.508 mm) and a channel radial thickness 48 in a range of from about 0.005 inch (0.127 mm) up about 0.010 inch (0.254 mm). Moreover, each longitudinal channel of the MIM tubing may have a width 50 in a range of from about 0.030 inch (0.762 mm) up to about 0.050 inch (1.270 mm).

Figure 14:
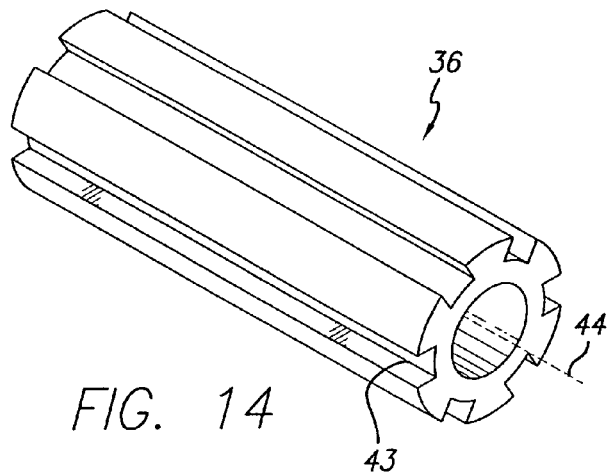
FIG. 14 is a longitudinal, plan view of MIM tubing having six channels arranged sixty degrees apart made in accordance with the present invention.

FIG. 14 is a longitudinal, plan view of an alternative embodiment of the MIM tubing 36 having six longitudinal channels 43 molded therein. The longitudinal channels may be arranged circumferentially around the MIM tubing such that they are set sixty degrees apart and parallel to the longitudinal axis 44.

Figure 15:
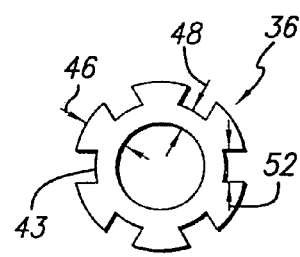
FIG. 15 is an enlarged, transverse, cross-sectional view of the MIM tubing of FIG. 14 made in accordance with the present invention.

FIG. 15 illustrates an enlarged, transverse, cross-sectional view of the MIM tubing 36 of FIG. 14. The radial thickness 46 of the MIM tubing and the corresponding channel radial thickness 48 may be equal to the corresponding dimensions for the preceding embodiment having four longitudinal channels 42 molded therein. Each longitudinal channel 43 of the MIM tubing may have a width 52 in a range of from about 0.020 inch (0.508 mm) up to about 0.030 inch (0.762 mm).

Figure 16:
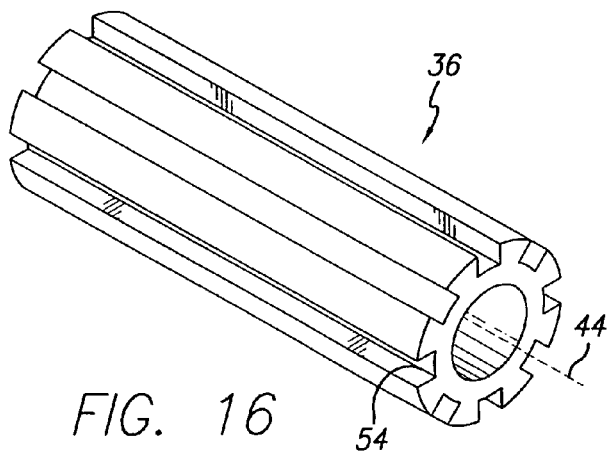
FIG. 16 is a longitudinal, plan view of MIM tubing having eight channels arranged forty-five degrees apart made in accordance with the present invention.

FIG. 16 is a longitudinal, plan view of an alternative embodiment of the MIM tubing having eight longitudinal channels 54 molded therein. The longitudinal channels may be arranged circumferentially around the MIM tubing such that they are set forty-five degrees apart and parallel to the longitudinal axis 44.

Figure 17:
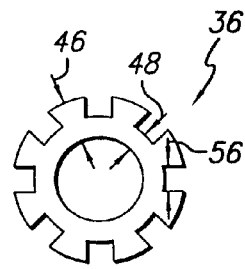
FIG. 17 is an enlarged, transverse, cross-sectional view of the MIM tubing of FIG. 16 made in accordance with the present invention.

FIG. 17 illustrates an enlarged, transverse, cross-sectional view of the MIM tubing of FIG. 16. The radial thickness 46 of the MIM tubing and the corresponding channel radial thickness 48 of the eight longitudinal channels 54 molded therein may be equal to the dimensions of the preceding embodiments. Each longitudinal channel of the MIM tubing may have a width 56 in a range of from about 0.010 inch (0.254 mm) up to about 0.020 inch (0.508 mm).

Figure 18:
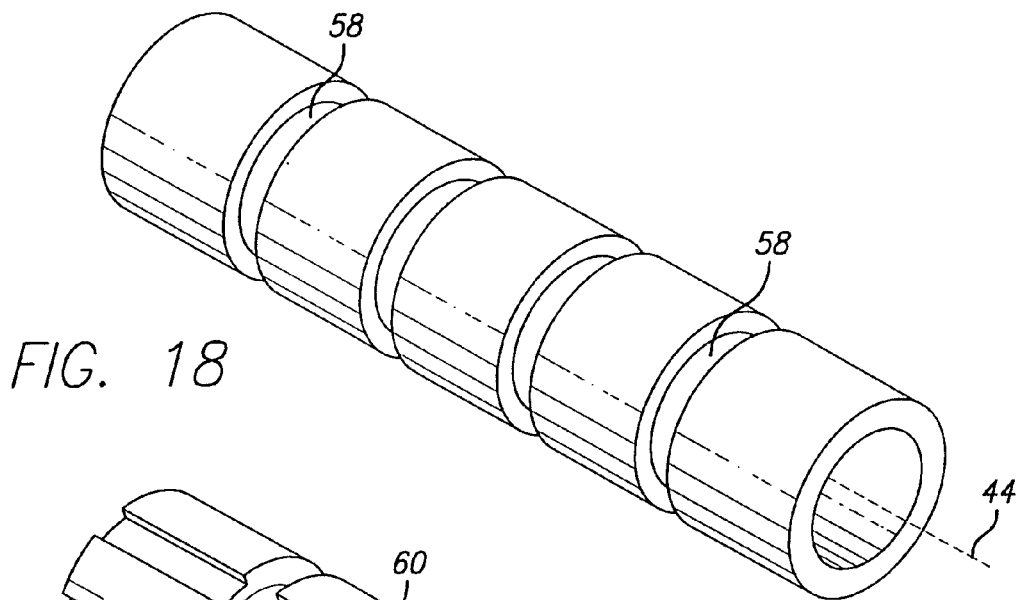
FIG. 18 is a longitudinal, plan view of MIM tubing having circumferential channels made in accordance with the present invention.

FIG. 18 is a longitudinal, plan view of an alternative embodiment of MIM tubing having a plurality of circumferential channels 58 molded therein. The plurality of circumferential channels may be arranged around the MIM tubing such that the channels are set perpendicular to the longitudinal axis 44. It can be appreciated by the present invention that the plurality of circumferential channels can be molded into the tubing in any number of variations and is not limited to the configuration shown in FIG. 18. Regarding the dimensions of the plurality of circumferential channels, each circumferential channel may have a radial thickness in a range of from about 0.010 (0.254 mm) inch up to about 0.020 inch (0.508 mm) and a width in a range of from about 0.030 inch (0.762 mm) up to about 0.050 inch (1.270 mm).

Figure 19:
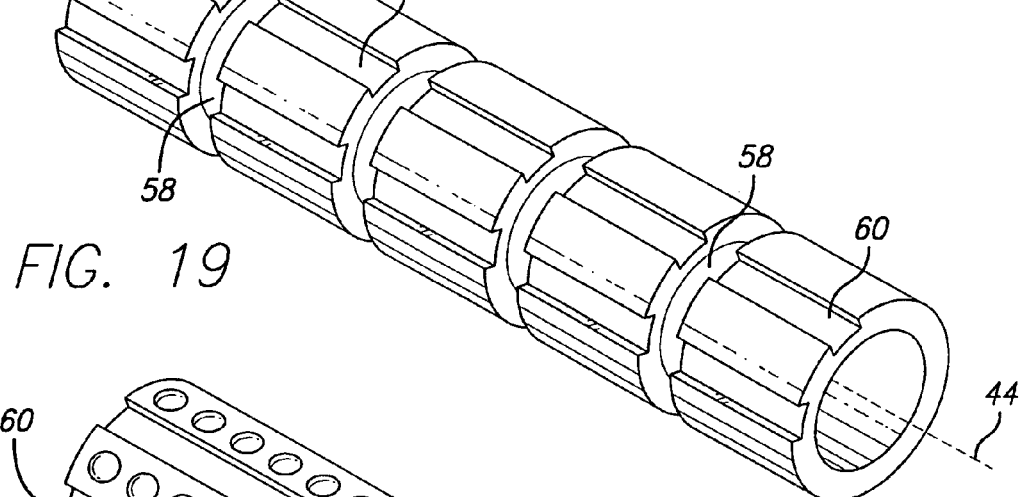
FIG. 19 is a longitudinal, plan view of MIM tubing having a combination of circumferential channels and longitudinal channels made in accordance with the present invention.

FIG. 19 is a longitudinal, plan view of an alternative embodiment of MIM tubing having a combination of circumferential channels 58 and longitudinal channels 60 molded therein. The arrangement of the longitudinal channels and circumferential channels combination can be modified according to the intended procedure, anatomy, and usage of the resultant stent, which is formed from the MIM tubing.

Figure 20A:
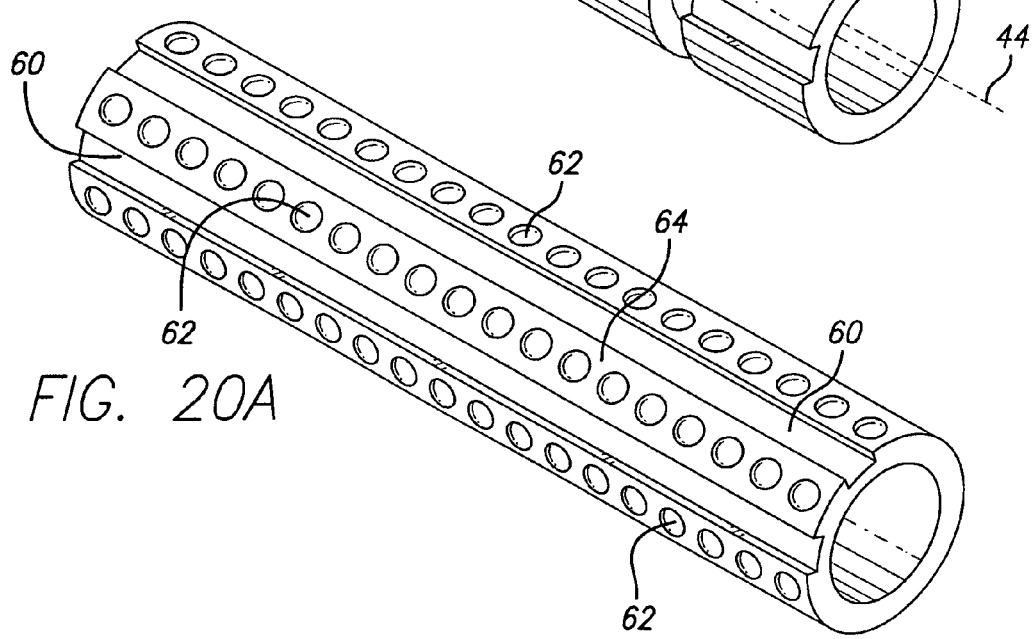
FIG. 20A is a longitudinal, plan view of MIM tubing having a combination of longitudinal channels and rounded depots made in accordance with the present invention.
Figure 20B:
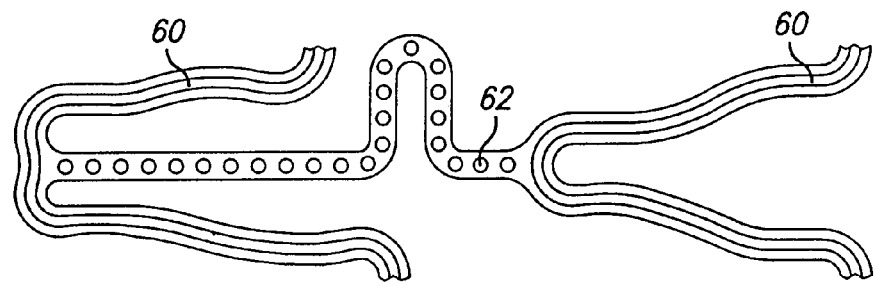
FIG. 20B is an enlarged partial view of a stent cylindrical ring-and-link design formed from the MIM tubing of FIG. 20A.

FIG. 20A is a longitudinal, plan view of yet another alternative embodiment of MIM tubing having a combination of longitudinal channels 60 and rounded depots 62 molded therein. An enlarged partial view of a stent cylindrical ring-and-link design formed from the MIM tubing of FIG. 20A is illustrated in FIG. 20B. It can be appreciated that the number of longitudinal channels molded into the outside surface 64 of the MIM tubing can be according to any of the preceding embodiments. Further, in metal injection molding depots on the outside surface of the tubing, the overall porosity of the resultant stent may be considered for determining the size, geometry, and concentration of the depots. Porosity is referred to as the total volume of pores in the stent body divided by the total volume of structural material of the stent. The capacity of substance that can be loaded into a stent of predetermined dimensions is determined by porosity. A stent having too high of a porosity can adversely affect the elasticity, strength, and structural integrity of the stent. It should be appreciated that stent design includes consideration of a tradeoff between strength, on one hand, and stent profile and stent load capacity on the other hand.

Depots 62 can be formed to accommodate virtually any stent design and are not limited to the design shown in FIGS. 20A-B. It is known that depots can be used for carrying a variety of substances, including, but not limited to, therapeutic substances, polymers impregnated with therapeutic substances, radioactive isotopes, and radiopaque materials. The arrangement of depots may vary according to the intended usage and application of the resultant stent. Depots may be formed by the manufacturer in accordance with MIM technology at any preselected location and have any preselected depth, size, and geometrical configuration. For example, depots may assume a variety of geometrical shapes, including, but not limited to, circular, square, rectangular, trapezoidal, and triangular shapes. It is contemplated by the present invention that depots are evenly distributed throughout the stent and have an equal volume so that the tissue in contact with the stent receives an equal distribution of therapeutic substance. Depth of depots is generally varied in proportion to the thickness of the stent as well as the clinical purpose and usage.

As one example, for a stent that carries a therapeutic substance or a polymer carrier impregnated with a therapeutic substance, a suitable depot or pore depth has a range of from about 10% to about 90% of the stent radial thickness. Generally, a depth not greater than about 50% of the stent radial thickness is most suitable. The specific depth of depots 62 depends on the amount of therapeutic substance deposited in the depots. In one embodiment of the present invention, the depots may have a depth of about 0.002 inch (0.051 mm), which is about one half the radial thickness of the MIM tubing or resultant stent.

As set forth previously, depots 62 may be formed in accordance with a variety of select geometrical shapes. As shown in FIG. 20B, the depots have a generally cylindrical shape. A diameter D of each cylindrical depot typically has a range of from about 10% up to about 90% of a width W of each cylindrical stent ring, although the diameter is usually not greater than about 80% of the ring width. The specific diameter depends on the application and purpose of the respective depots. The upper limit of the diameter may vary depending on material characteristics such as the hardness of the stent.

It can be appreciated that the depth and diameter of the individual depots formed within the outside surface 64 of the MIM tubing can vary relative to one another if desired. For example, the manufacturer using MIM technology can selectively control the volume of depots 62 on different positions of the outside surface of MIM tubing, either selectively varying the volume or making the volume consistent throughout the outside surface. In most applications, consistent depot volume is important for delivery of a therapeutic substance to insure that the substance is evenly distributed throughout the stent and results in consistent application of the therapeutic substance to the tissues in contact with the surface of the stent.

Figure 21:
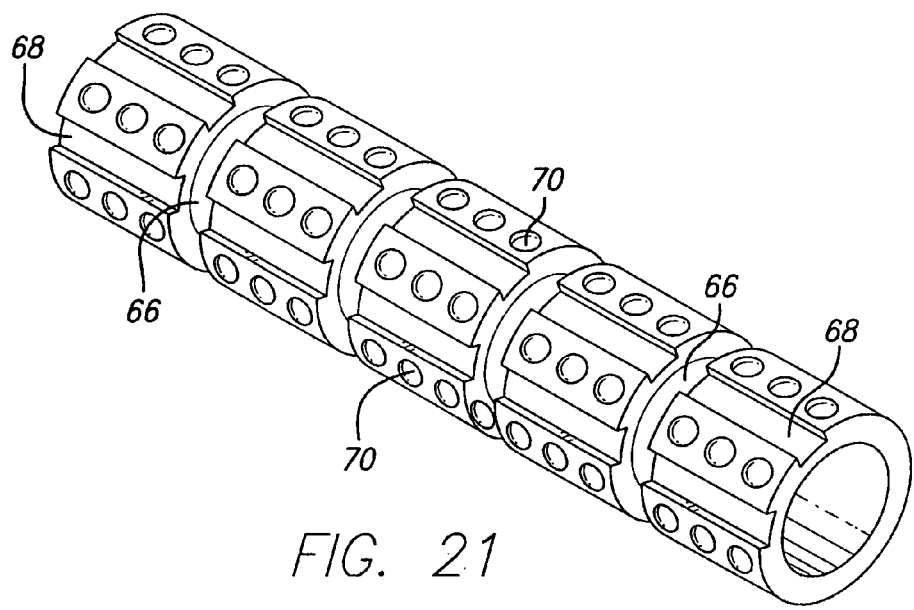
FIG. 21 is a longitudinal, plan view of MIM tubing having a combination of circumferential and longitudinal channels and rounded depots made in accordance with the present invention.

FIG. 21 is a longitudinal, plan view of an alternative embodiment of MIM tubing having a combination of circumferential channels 66 and longitudinal channels 68 and rounded depots 70 molded therein, which may be subsequently manufactured into a stent. This embodiment provides for optimal storage of a therapeutic drug if increased storage is desired for a particular application. Suitable dimensions of the aforementioned elements (e.g., circumferential channels, longitudinal channels, and rounded depots) may be configured in accordance with any one of the preceding embodiments.

In another embodiment of the present invention, a method of forming an intravascular stent having drug-eluting capabilities utilizing the manufacturing process of metal injection molding is disclosed herein. The present invention stent formed from metal injection molded tubing is able to store substantial amounts of therapeutic drug for the eventual release thereof at a treatment site. The method involves mixing a base material with a binding material to form a mixture. The mixture is molded into a shape by injecting the mixture into a geometric die. The die is configured to form a tube having an inside diameter and an outside diameter and a plurality of longitudinal channels arranged circumferentially around the tubing while set parallel to a longitudinal axis of the stent. A pressure force is applied to the mixture at an appropriate pressure which is known in the art. After proceeding with standard MIM processes to the mixture including the steps of debinderizing and sintering as set forth above, a stent pattern is formed by laser machining and electro-polishing the tubing with circumferential rings interconnected by links. Finally, the plurality of longitudinal channels are loaded with at least one therapeutic drug. In other embodiments of the present invention, different types of therapeutic drugs can be used in combination with each other in the longitudinal channels of the stent. For example, adjacent longitudinal channels can also be loaded with different types of therapeutic drug such that alternating longitudinal channels contain the same therapeutic drug.

In a further embodiment of the present invention, the tubing formed in the previous embodiment can have a plurality of circumferential channels molded therein that are configured to be perpendicular to the stent longitudinal axis. In addition, a plurality of depots can be molded in various areas of an outside surface of the tubing, preferably in the areas surrounding the longitudinal and/or circumferential channels of the stent.

In other embodiments of the present invention, different types of therapeutic drugs may be used in combination with each other for localized drug therapy in a blood vessel. For example, the longitudinal channels may be loaded with a therapeutic drug that is of a different type than that used in the depots.

Various therapeutic agents, drugs and other pharmacologic compounds may be loaded into the longitudinal channels, circumferential channels, and/or depots of the stent and delivered to the target site in the vasculature. Classes of such compounds include, but are not limited to, substances that are antiproliferative, antithrombogenic, antineoplastic, antiinflammatory, antiplatelet, anticoagulant, antifibrin, antithrombin, antimitotic, antibiotic, and antioxidant. Specific examples of therapeutic agents or drugs that are suitable for use in accordance with the present invention include taxol, paclitaxel, docetaxel, sirolimus, everolimus, actinomycin D (ActD), prostaglandins, aspirin or derivatives and analogs thereof.

Examples of antiplatelets, anticoagulants, antifibrins, and f antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B (an antiplatelet drug from Centocor located in Malvern, Pa.). Examples of antimitotic agents include methotrexate, azathioprine, vincristine, vinblastine, fluorouracil, adriamycin, and mutamycin.

Examples of cytostatic or antiproliferative agents include angiopeptin (a somatostatin analog from Ibsen located in the United Kingdom), angiotensin converting enzyme inhibitors such as CAPTOPRIL (available from Squibb located in New York, N.Y.), CILAZAPRIL (available from Hoffman-LaRoche located in Basel, Switzerland), or LISINOPRIL (available from Merck located in Whitehouse Station, N.J.), calcium channel blockers (such as nifedipine), colchicine, fibroblast growth factor (FGF) antagonists, fish oil (omega 3-fatty acid), histamine antagonists, LOVASTATIN (an inhibitor of HMG-CoA reductase, a cholesterol lowering drug from Merck), methotrexate, monoclonal antibodies [such as platelet-derived growth factor (PDGF) receptors], nitroprusside, phosphodiesterase inhibitors, prostaglandin inhibitor (available from GlaxoSmithKline located in United Kingdom), seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other types of drugs may be developed which are equally applicable for use with the present invention. The treatment of diseases using the above therapeutic agents is known in the art. The calculation of dosages, dosage rates and appropriate duration of treatment are previously known in the art. Furthermore, the drugs or agents are loaded at desired concentration levels per methods well known in the art to render the device ready for implantation. A thin polymeric coat layer can be disposed over the surface of the stent to cover the longitudinal and circumferential channels and depots molded therein. The polymeric coating forms a membrane that reduces the rate of release of the therapeutic drug from the channels and/or depots.

In use, the drug-eluting stent is deployed using conventional techniques. Once in position, the drug gradually diffuses into adjacent tissue at a rate dictated by the parameters associated with any polymer coat layer. The total dosage that is delivered is limited by the total amount of the drug that had been loaded within the longitudinal and circumferential channels and depots of the stent. The drug is selected to treat the deployment site and/or locations downstream thereof. For example, deployment in the carotid artery will serve to deliver such drug to the brain.

The illustrative stent of the present invention can be made in many ways. One method of making such a stent is to cut tubing of biocompatible material formed according to the method of the present invention so as to remove portions of the tubing in the desired pattern for the stent, leaving relatively untouched the portions of the MIM tubing that are to form, for example, the cylindrical rings 11 and links 17. Since the finished product stent diameter is very small, the tubing from which the medical device is made must necessarily also have a small diameter. Typically the MIM tubing from which the medical device is made has an outer diameter on the order of about 0.04 inches (1.02 mm) and 0.4 inches (10.2 mm) in the unexpanded condition, and can be expanded to an outer diameter of about 0.1 inch (2.5 mm) or more. The wall thickness of the tubing is typically in the range of about 0.002 inch (0.051 mm) to 0.01 inch (0.25 mm). Various processes of forming the desired stent pattern are available and are known in the art, such as, but not limited to, using laser or chemical etching, or electronic discharge machining. The foregoing stent dimensions can vary substantially in size and shape so that the disclosed dimensions and shapes are representative examples only and are not meant to be limiting.

Figure 22:
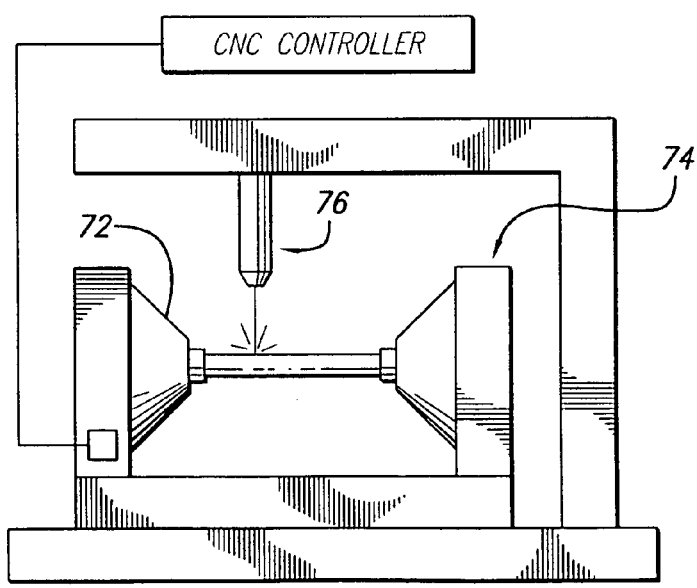
FIG. 22 is a schematic representation of equipment for laser cutting tubing in the manufacture of stents in accordance with the present invention.

After forming the tubing 36 using MIM technology in accordance with the present invention, the tubing may be cut in the desired pattern by using a machine-controlled laser, as illustrated schematically in FIG. 22. The tubing may put in a rotatable collet fixture 72 of a machine-controlled apparatus 74 for positioning the tubing relative to a machine-controlled laser 76, utilizing a computerized numeric controller (CNC). According to machine-encoded instructions, the tubing is rotated and moved longitudinally relative to the laser. The laser selectively removes material from the tubing by ablation, and a desired pattern is cut into the tubing.

Cutting a fine structure via a machine-controlled laser requires minimal heat input and the ability to manipulate the tubing with precision. It is also necessary to support the tubing, yet not allow the tubing to distort during the cutting operation. In one embodiment of the present invention, the tubing is made of stainless steel with an outside diameter of about 0.060 inch (1.524 mm) to 0.095 inch (2.413 mm) and a wall thickness of about 0.002 inch (0.051 mm) to 0.01 inch (0.25 mm). To achieve a relatively small geometry of a desired stent pattern formed with ring struts 11 and links 17 having a width of about 0.0035 inch (0.0889 mm), it is necessary to have very precise control of the laser's power level, focused spot size and positioning of the laser cutting path. After laser cutting, the stent may be surface modified in a variety of manners well known in the art, not limited to bead blasting, etching, and electropolishing. The present invention contemplates that the MIM device can be further machined (e.g., laser cutting) to refine the longitudinal channels and circumferential channels and struts.

The foregoing laser cutting process to form the cylindrical rings 11 can be used with stainless steel and metals, such as cobalt-chromium, titanium, tantalum, platinum, nickel-titanium, zirconium and alloys thereof, that are suitable for use in humans, and typically used for intravascular stents. Further, while the formation of the cylindrical rings is described above, other processes of forming the rings are possible and are known in the art, such as by using chemical etching, electronic discharge machining, stamping, and other processes.

While particular forms of the invention have been illustrated and described, it will also be apparent to those skilled in the art that various modifications and improvements can be made without departing from the spirit and scope of the invention. More specifically, it should be clear that the present invention is not limited to the medical devices described herein, and may be used to form various other types of medical devices. Accordingly, it is not intended that the invention be limited, except as by the appended claims.

What is claimed is:

1. An intravascular stent for controlled storage and release of therapeutic drugs and for delivery of the therapeutic drugs in localized drug therapy in a blood vessel, comprising:
   a longitudinal axis; and
   tubing centered about said longitudinal axis having a pattern formed therein defining circumferential rings interconnected by links, the tubing having an inside diameter, an outside diameter and wherein a plurality of longitudinal channels are formed therein, each channel having a length, width and depth and wherein such channels are arranged so as to be circumferentially spaced about said tubing and such that their lengths extend parallel to the longitudinal axis, the tubing being formed of a base material in the form of a powder that is metal injection molded.

2. The stent of claim 1, wherein the base material comprises a mixture of a metallic powder, a thermoplastic powder, and binder materials.

3. The stent of claim 2, wherein the metallic powder comprises at least one of stainless steel, nitinol and cobalt-chromium alloy.

4. The stent of claim 2, wherein the metallic powder comprises an element or alloy sufficiently radiopaque for x-ray imaging.

5. The stent of claim 4, wherein the element or alloy comprises one of tantalum, titanium, tungsten and zirconium.

6. The stent of claim 2, wherein the metallic powder comprises a magnetic resonance imaging (MRI) compatible element or alloy.

7. The stent of claim 2, wherein the base material comprises about 40% metallic powder and about 60% thermoplastic powder.

8. The stent of claim 1, wherein the inside diameter is substantially uniform along the length of the tubing.

9. The stent of claim 1, wherein the plurality of longitudinal channels have a wall that at least partially encapsulates the therapeutic drug stored therein.

10. The stent of claim 9, wherein the therapeutic drug is selected from the group consisting of antiplatelets, anticoagulants, antifibrins, antiinflammatories, antithrombins, and antiproliferatives.

11. The stent of claim 1, wherein the plurality of longitudinal channels arranged circumferentially around the tubing includes four channels set ninety degrees apart.

12. The stent of claim 1, wherein the depth of the plurality of longitudinal channels ranges from about 0.002 inch (0.051 mm) up to about 0.005 inch (0.127 mm).

13. The stent of claim 1, wherein the width of the plurality of longitudinal channels ranges from about 0.010 inch (0.254 mm) up to about 0.030 inch (0.762 mm).

14. The stent of claim 1, wherein the depth and width of the longitudinal channels can be modified in order to increase storage of the therapeutic drug therein.

15. The stent of claim 1, wherein the tubing is nanoporous.

16. The stent of claim 15 further comprising a therapeutic drug loaded within the pores of the nanoporous tubing.

17. The stent of claim 1, wherein the base material comprises a powder with a particle size and a pressure force aspect of molding and a temperature/time aspect of sintering being selected in view of the particle size such that the resultant tubing is nanoporous.

18. The stent of claim 1, wherein the tubing has a porosity in a range of from about 92% to about 99% dense.

19. The stent of claim 1, wherein the stent has a strut thickness in a range of from about 0.0022 inch (0.0559 mm) to about 0.0055 inch (0.1397 mm).

20. The stent of claim 1, wherein the stent has a strut width of about 0.0038 inch (0.0965 mm).

* * * * *